United States Patent

Humphrey et al.

Patent Number: 5,149,838
Date of Patent: Sep. 22, 1992

[54] INTERMEDIATES FOR SUBSTITUTED AZETIDINONES USEFUL AS ANTI-INFLAMMATORY AND ANTIDEGENERATIVE AGENTS

[75] Inventors: Guy R. Humphrey, Belle Mead; Ann M. Madar, Rahway; Andrew S. Thompson, Mountainside, all of N.J.

[73] Assignee: Merck & Co., Inc., Rahway, N.J.

[21] Appl. No.: 764,609

[22] Filed: Sep. 20, 1991

[51] Int. Cl.$^5$ .......................................... C07D 307/78
[52] U.S. Cl. .................................... 549/471
[58] Field of Search ......................... 549/471

[56] References Cited

U.S. PATENT DOCUMENTS 4,680,391  7/1987  Firestone et al. .................... 540/355

FOREIGN PATENT DOCUMENTS 0199630 10/1986 European Pat. Off. .
0337549 10/1989 European Pat. Off. .

OTHER PUBLICATIONS

Organic Synthesis, Coll. vol. 5, pp. 251–254 (1967).
Graalmann et al., Chem. Ber., vol. 117, pp. 2988–2997 (1984).
Lal et al., Tet. Letters, No. 23, pp. 1977–1980 (1977).
Yoshioka et al., Tet. Letters, vol. 30, No. 13, pp. 1657≅1660 (1989).

Primary Examiner—Bernard Dentz
Attorney, Agent, or Firm—Curtis C. Panzer; Raymond M. Speer

[57] ABSTRACT

Disclosed is a process for the enantioselective synthesis of the compound of Formula I and related compounds. The process comprises the synthesis of the benzofuranyl carboxaldehyde; introduction of the benzylic amine functionality with control of the absolute stereochemistry; preparation of the azetidinone fragment and its coupling to the benzofuranyl amine fragments. The carboxylic acid in Formula I is liberated using heterogenous palladium catalyzed de-allylation of the allyl esters. Compounds I have been found to be potent elastase inhibitors and thereby useful anti-inflammatory and antidegenerative agents.

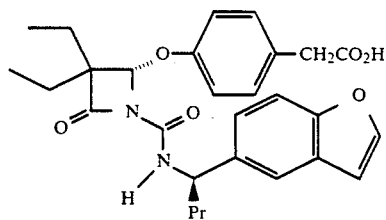

I

1 Claim, No Drawings

INTERMEDIATES FOR SUBSTITUTED AZETIDINONES USEFUL AS ANTI-INFLAMMATORY AND ANTIDEGENERATIVE AGENTS

BACKGROUND OF THE INVENTION

Substituted azetidinones of the following general formula

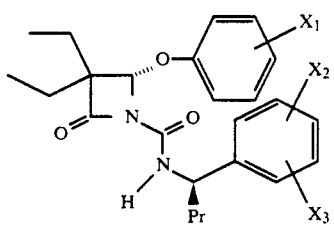

have been found to be useful as anti-inflammatory and anti-degenerative agents. Their utility in treating human leukocyte elastase mediated diseases and their method of preparation is disclosed in EPO 337,549 published Oct. 18, 1989, which reference is hereby incorporated by reference.

The prior art comprises:

Tetrahedron Letters pp. 1977 (1977) which discloses intermolecular dehydration reaction occuring between alcohols and acidic portion of the subject molecule on treatment with diethyl azodicarboxylate and triphenyl phosphine under neutral conditions [i.e., the Mitsunobu Reaction]; Tetrahedron Letters Vol. 30 (13) pp. 1657-60 (1989) which discloses the use of chiral catalysts;

Chem. Ber. Vol. 117 pp. 2988-2997 (1984); Bull. Chem. Soc. Jpn. Vol. 56 p. 2762 (1983); and Org. Syn. Coll. Vol. 5 pp. 251 which disclose benzofuran synthesis via the Perkin reaction.

The instant invention represents an important advance over the art. For example, Applicants have suprisingly achieved excellent control of absolute stereo chemistry in a Mitsunobu azide displacement on an electron rich benzylic alcohol.

BRIEF DESCRIPTION OF THE INVENTION

Disclosed is a process for the enantioselective synthesis of compounds of Formula II and specifically compound of Formula I.

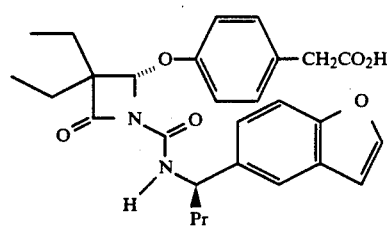

The process comprises synthesis the benzofuranyl carboxaldehyde; introduction of the benzylic amine functionality with control of the absolute stereochemistry; preparation of the azetidinone fragment and its coupling to the benzofuranyl amine fragments; followed by heterogenous palladium catalyzed deallylation. These compounds have been found to be potent elastase inhibitors and thereby useful anti-inflammatory and antidegenerative agents.

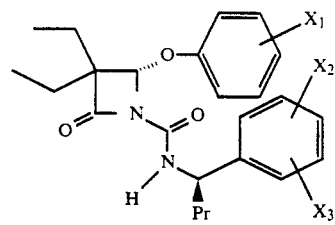

DETAILED DESCRIPTION OF THE INVENTION

In a first embodiment the instant invention concerns a process of preparing a compound of Formula I

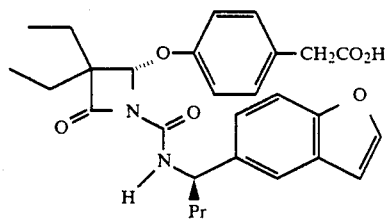

comprising the steps of
(a) reacting the hydrochloride salt of Compound C

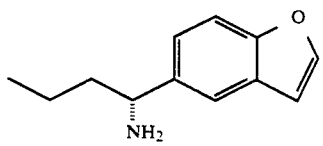

in a solvent selected from the group comprising a aromatic solvent, a $C_{1-6}$alkylacetate or an ether, with phosgene to yield Compound D

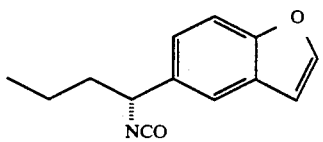

For purposes of the specification, aromatic solvents include, but are not limited to, benzene, toluene and xylene, preferably toluene. Similarly, $C_{1-6}$alkylacetate is intended to include but is not limited to ethylacetate. Similarly, for purposes of this specification, etheral solvents include, but are not limited to ethers such as diethyl ether di-n-butyl and diisopentyl ethers, anisole, cyclic ethers such as tetrahydropyran, 4-methyl-1,3-dioxane, dihydropyran, tetrahydrofurfuryl methyl ether, ethyl ether, furan, tetrahydrofuran and 2-ethoxytetrahydrofuran. For complete reaction the molar ratio of hydrochloride to phosgene should be approximately 1 to 1, or larger; preferably about 1 to 3. The reaction may be conducted from 50° C. to 125° C., preferably 80° C. to 100° C. The reaction is allowed to proceed until substantially complete in about 1 to 2 hours; and b) Reacting the Compound D in an aprotic solvent with Compound E

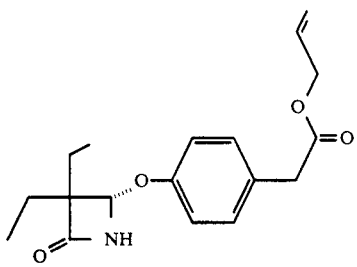

To yield, after deblocking a compound of Formula I.

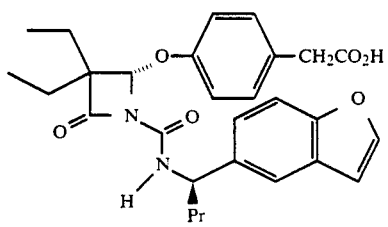

For purposes of this specification the aprotic solvent includes, but is not limited to N,N-diC$_{1-6}$ alkylcarbonyl amide, such as N,N-dimethyl formamide (DMF) or toluene, tetrahydrofuran (THF), and dichloromethane; DMF is preferred. The molar ratio of Compound D to compound E should be approximately 1 to 1. The reaction is allowed to proceed substantially complete in about 0.5 to 2 hours.

The reaction may be conducted at from $-20°$ to $+80°$ C.

Methods of deblocking the alkyl group are well known in the art. See Protective Groups In Organic Synthesis, T. Greene, 1981. Applicants have found homogenous and heterogenous catalytic deblocking useful. As is well known homogenous deblocking can be accomplished by use of Pd(PPh$_3$)$_4$ in the presence of acetic acid or amines. See Palladium Reagents In Organic Synthesis R. F. Heck pp 423-433 1985. Applicants have found heterogeneous catalysis to be of suprising superiority. For example, the homogeneous reaction would not go to completion, the palladium source was an unstable and expensive entity and deposited palladium in the batch.

The heterogeneous reaction, on the other hand, used readily available Pd(c), the reaction would go to completion and no palladium residue was deposited in the batch. Heterogeneous deallylations are rare, and in this case, the benzofuran contains a reducible olefinic bond.

For purposes of this specification heterogeneous catalysis shall be defined to include use of metals such as but not limited to palladium, platinum or rhodium supported on an inert substrate such as carbon or alumina in the presence of a hydrogen donor e.g. hydrogen gas, formic acid, ammonium formate. See Chem. Rev., 1985, 85 129-170.

In one class of the first embodiment the process further comprises a') Mitsunobu conversion of the alcohol, Compound B

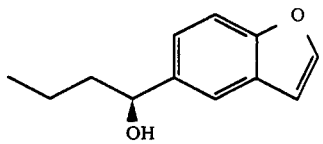

to the amine, Compound C

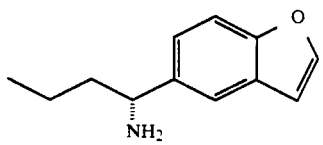

For purposes of this specification, Mitsunobu conversion is defined as the incorporation of either a phthalimide or azide at the hydroxy of compound B which is thereafter incorporated into the amine of compound C. The route is summarized in Scheme II

SCHEME II

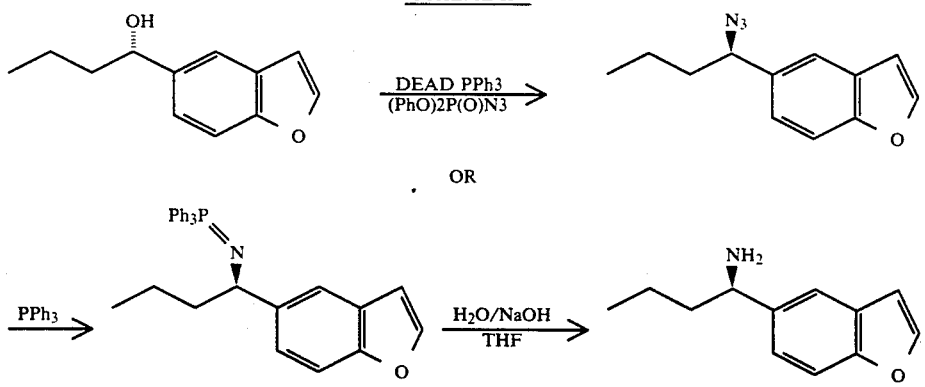

The molar ratio of the compound B to the azide is approximately 1:1. The molar ratio of compound B to diethylazodicarboxylate is approximately 1:2. The reaction can be conducted at $-25°$ to $+25°$ C., and is allowed to proceed until essentially complete.

Investigation of the Mitsunobu reaction with diphenylphosphoryl azide as the azide source revealed a number of limitations to the standard reagent addition sequence. Consequently, two procedures were investigated which were compatible with these limitations. In the first procedure triphenylphosphine was added to a mixture of Compound B, DEAD and azide reagent. After in-situ iminophosphorane formation and hydrolysis, the amine C was isolated and the enantiomeric excess determined (HPLC or GC of menthylcarbamates). In THF the yield range was 40-50% with ee=56-76%. In toluene the yield was somewhat lower (24%) with ee=84%.

The second procedure involved preformation of the Mitsunobu reagent (DEAD and triphenylphosphine) in THF, addition of the azide reagent to the resultant slurry and then slow addition of the alcohol B. The amount of unsaturated by-product and ee % of isolated amine C was markedly effected by the addition rate.

Isolation of the product amine C by silica gel chromatography gave a 71% yield (88% ee). Using the same reaction conditions but changing the isolation procedure to an acid/base extraction resulted in a 40-50% yield of amine C (also 88% ee).

Within this class the first embodiment further comprises

Chiral catalytic addition to the aldehyde, Compound A

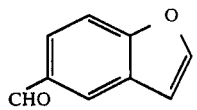

by reaction with di-$C_{1-6}$alkyl zinc in an aromatic solvent, as defined above.

To yield the alcohol, Compound B

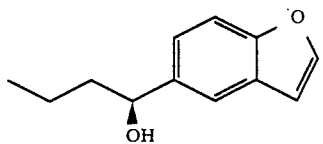

For purposes of this reaction di-$C_{1-6}$alkyl-zinc is intended to include, but not limited to Di-n-propylzinc, which is commercially available.

The molar ratio of aldehyde to di-$C_{1-6}$alkyl-zinc should be approximately 1:1 or less. The reaction may be conducted at from −25° to 25° C.

Asymmetric Dipropylzinc Addition

The literature contains many examples of chiral catalysts capable of accelerating the rate of dialkylzinc addition to aldehydes to afford chiral secondary alcohols. A catalyst system based on transdiaminocyclohexane derivatives was described by Yoshioka (T.L. 1989). We have found that, when modified, this system possesses certain unexpected advantages; in particular, catalyst loadings down to 0.05 mol % gave excellent enantioselectivity (ee 98%).

In a second embodiment the invention concerns a process for preparing the compound X

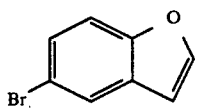

by an improved Perkin type reaction. The improvement comprising controlled addition of acetic anhydride to a prepared solution of the acid Y.

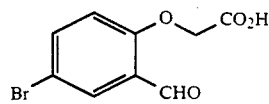

The applicants have unexpectedly found that the yield of compound X can be dramatically increased to 85% (as compared to 40% obtained by using prior art procedures which requires addition of all of the reagents and heating to reflux for a specified period of time) when the acetic anhydride is added in small aliquots over an extended period of time. Dropwise addition over 6 hours has proven particularly useful. Alternatives to use of the acetic anhydride include propionic acid, sodium propionate and propionic anhydride. Moreover very slow addition of acetic anhydride (2-4) parts to a solution of acid 5 (1 part), sodium acetate (2 parts) in acetic acid (5 parts) gave high yields of the bromofuran (80 to 85%). The only by-product is 5-bromo-2-benzofurancarboxylic acid. Isolation of pure product by extraction into hexane is simple and attractive.

In one class the second embodiment further comprises alkylation of 5-bromosalicylaldehyde Z

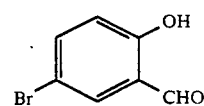

with bromoacetic acid in an etheral solvent in the presence of a base. To yield the compound Y

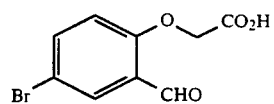

For purposes of this specification, bases are intended to include, but are not limited to alkali earth metal hydroxide, such as sodium, potassium or lithium hydroxide; preferably sodium hydroxide.

The reaction can be conducted at 20° to 100° C. This is allowed to proceed until essentially complete. The molar ratio of compound Z to bromoacetic acid is approximately 1:1; preferably with some excess of the acid. The molar ratio of compound Z to base is approximately 1:2.

In a third embodiment the invention concerns the process intermediates A, B, C and D, which are:

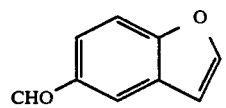

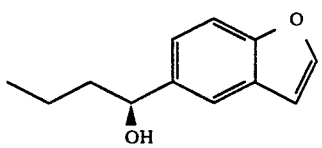

-continued
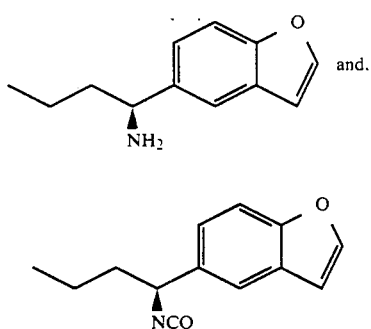
and,
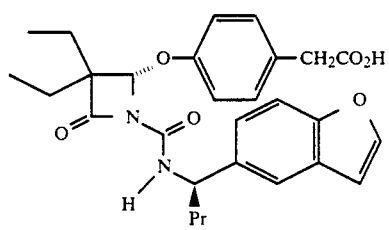
The overall scheme for production of compound I
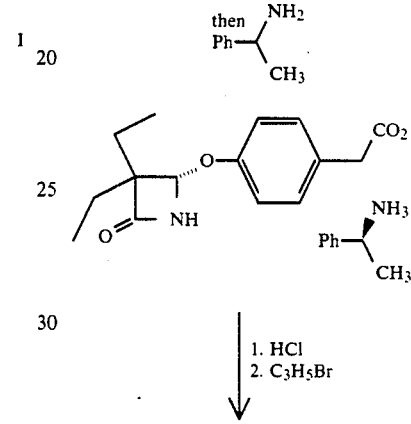
is shown in Scheme 1.
SCHEME 1
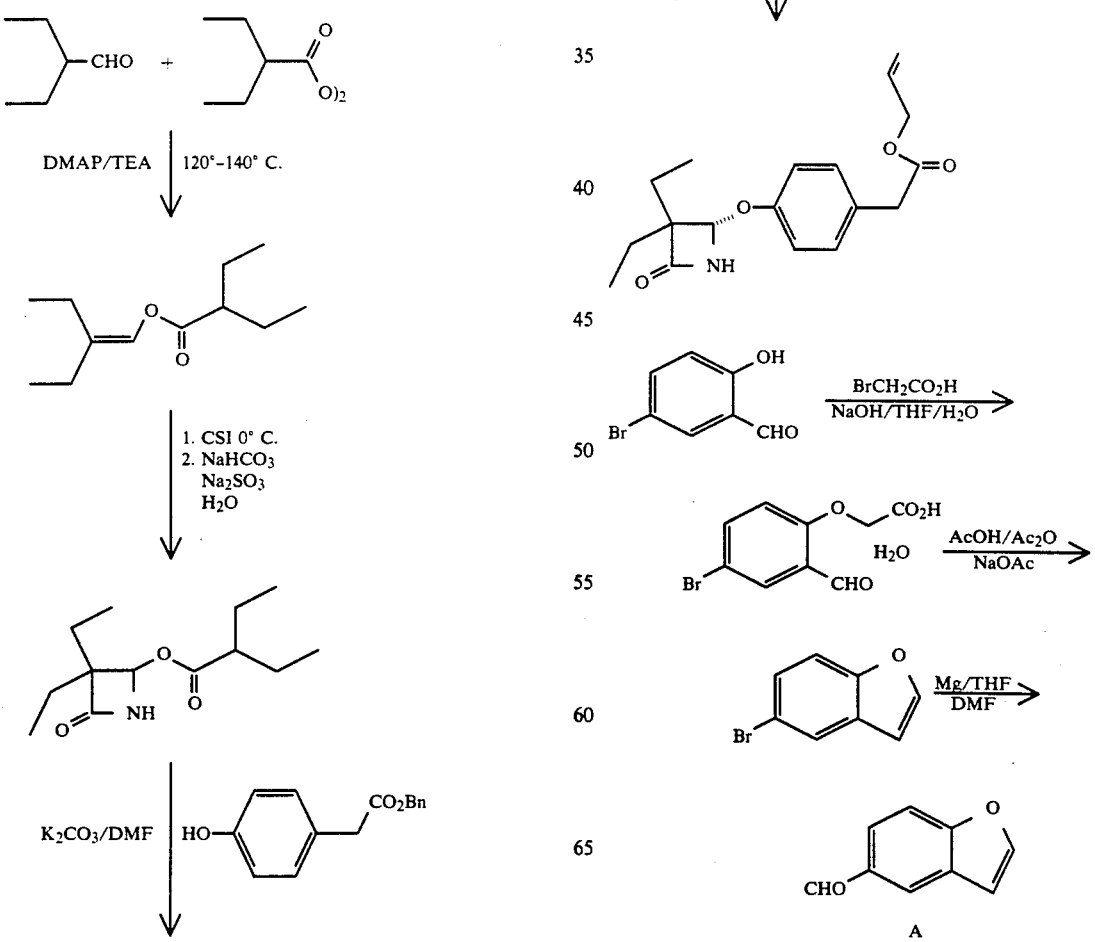
-continued
SCHEME 1
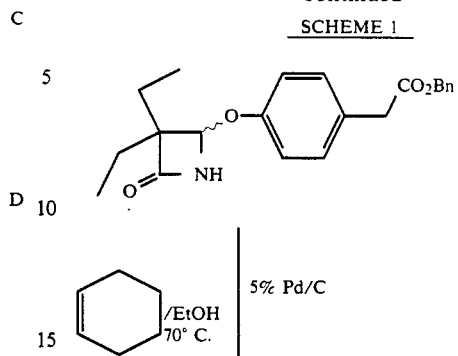

-continued
SCHEME 1

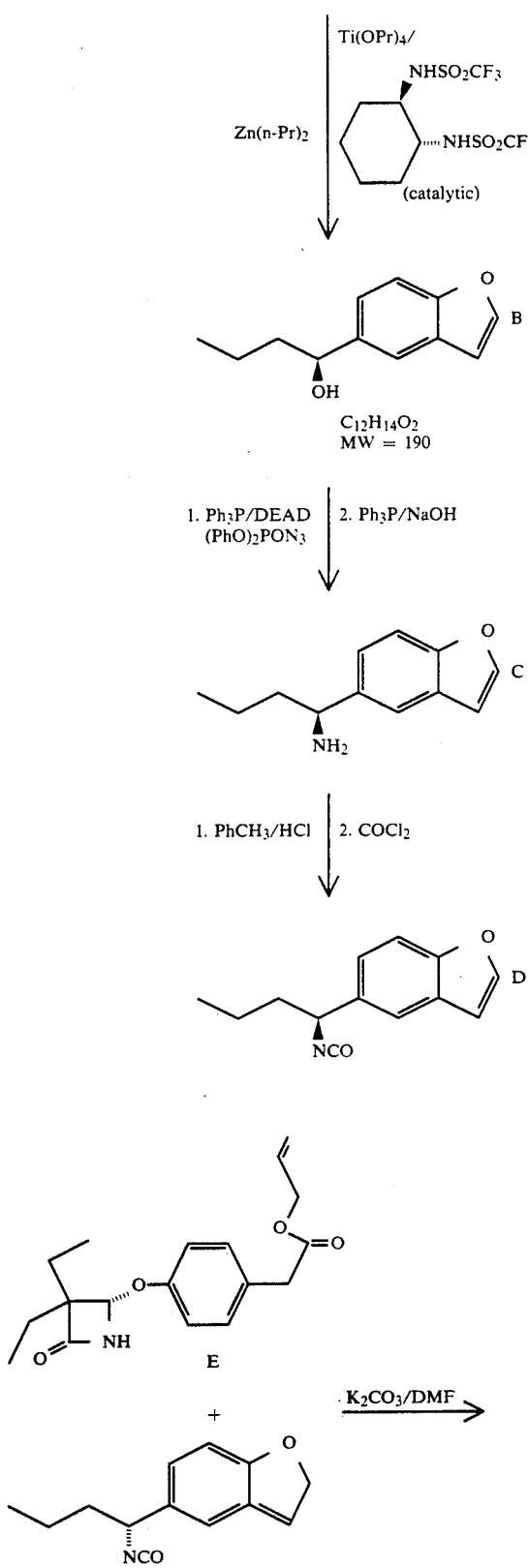

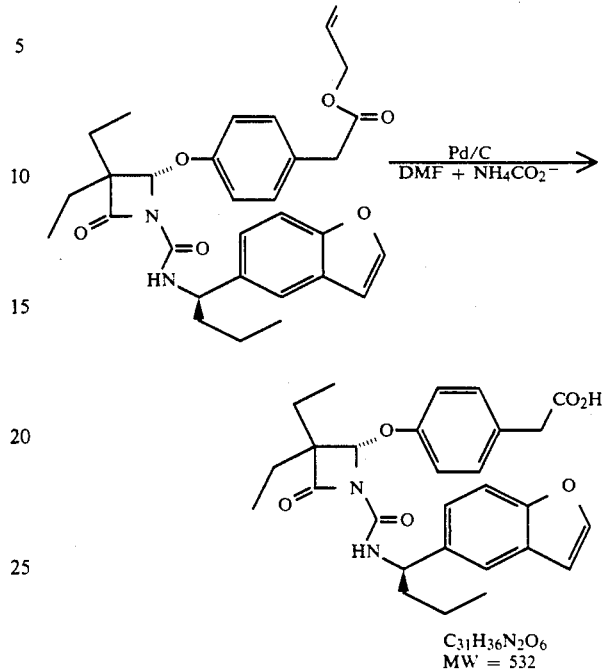

The following examples illustrate the process and intermediates of the invention and as such are not to be considered as limiting the invention as set forth in the claims appended hereto:

EXAMPLE 1

Preparation of allyl-4-((3,3-diethyl-4-oxo-2-azetidinyl)oxy-benzene acetate

Step A: Preparation of 4-Hydroxyphenylacetic Acid Benzyl Ester

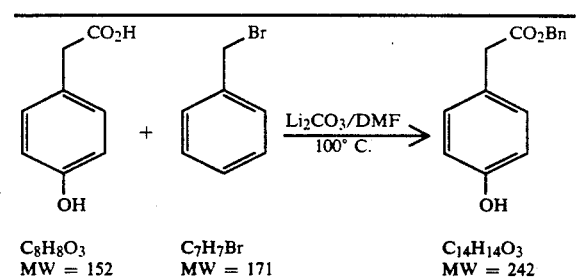

| | Amount | Mole | MW |
|---|---|---|---|
| 4-Hydroxyphenylacetic acid | 2.0 KG | 13.16 | 152 |
| Lithium carbonate | 1.07 kg | 14.46 | 74 |
| Benzyl Bromide (d = 1.438 g/mL) | 1.88 L | 15.81 | 171 |
| DMF (KF, 25 μg/mL) | 8 L | | |
| 2N Hydrochloric acid | 10 L | 20 | |
| Saturated aqueous sodium bicarbonate | 6 L | | |
| Ethyl acetate | 10 L | | |
| Toluene | 18 L | | |
| Hexanes | 12 L | | |

4-Hydroxyphenylacetic acid (2.0 kg) is dissolved in DMF (8 L) and lithium carbonate (1.07 kg) is added in one portion followed by benzyl bromide (1.88 L). The mixture is heated to 100° C. over 1 hour, aged for 3 hours. The mixture is cooled to 85° C. and transferred into a 50 L vessel and quenched with 2N HCl (10 L).

The mixture is extracted with ethyl acetate (2×5 L). The combined organic extracts are washed with saturated aqueous sodium bicarbonate (6 L) and D.I. water (3×6.5 L). Each wash with D.I. water causes an emulsion which is broken with toluene (approx. 1.5 L.).

The solvent is removed in vacuo to afford an off-white solid, which is dissolved in toluene (4 L) by heating to 60° C. After 1 L of solvent is removed in vacuo the temperature drops to 45° C. and crystallization begins. The batch is diluted with toluene (4 L) (temperature drops to 40° C.). Hexanes (8 L) are added and the slurry cooled to 25° C. and stirred for 18 hours. The batch is cooled to 10° C. and filtered, the cake is washed with cold 1:1 hexanes:toluene (2×3 L) and air-dried. The resulting off-white solid is dried in a vacuum oven at 50° C. with a $N_2$ purge for 20 h to afford 2.37 kg of an off-white solid for an isolated yield of 76%.

Step B: Preparation of
1-(2-ethylpropionyloxy)-2ethyl-1-butene

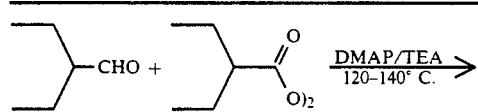

$C_6H_{12}O$  $C_{12}H_{22}O_4$
MW = 100  MW = 214

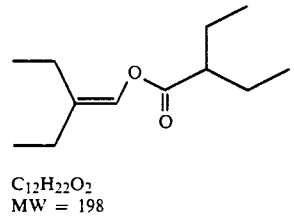

$C_{12}H_{22}O_2$
MW = 198

|  | Amount | Mole | MW |
|---|---|---|---|
| Anhydride (d = 0.927) | 4.34 L | 18.8 | 214 |
| Aldehyde (d = 0.814) | 2.28 L | 18.55 | 100 |
| 4-Dimethylaminopyridine | 210 gm | 1.72 | 122 |
| Triethylamine (d = 0.726) | 2.62 L | 18.8 | 101 |
| D.I. water | 5 L |  |  |
| Hexanes | 2.5 L |  |  |
| Ethyl acetate | 1.3 L |  |  |
| 2N HCl | 3 L | 6.0 |  |
| Satd. NaHCO$_3$ | 6 L |  |  |

A 22 L flask with an overhead stirrer and an $N_2$ inlet is charged with 2-ethylbutyric anhydride (4.34 L), 2-ethylbutyraldehyde (2.28 L), triethylamine (2.62 L) and 4-dimethylaminopyridine (210 gm). The mixture is warmed to 120° C. over approximately 1.5 hours. The temperature of the mixture is adjusted to 140° C. over 8 hours. The mixture is then stirred at 140° C. for 10 hours. The mixture is then cooled to 90° C. D.I. water (2 L) is added and the mixture heated to reflux (95°-96° C.) for 1 hour. The mixture is cooled to +25° C.

The mixture is poured into a 22 L extractor and to this is added D.I. water (2 L) and 3:1 hexanes:ethyl acetate (3 L). The mixture is stirred and the aqueous layer removed. The organic is washed sequentially with cold 2N HCl (3 L) and saturated NaHCO$_3$ (3×2 L). The organic is concentrated in vacuo then flushed with ethyl acetate (500 mL). This affords 3.7 kg of a yellow oil. The product is purified by simple distillation;

B.P. = 80° C./1 mm, to give 3.3 kg of a clear colorless oil, 89% yield.

Step C: Preparation of
4-(2-ethylpropionyloxy)-3,3-diethylazetidin-2-one

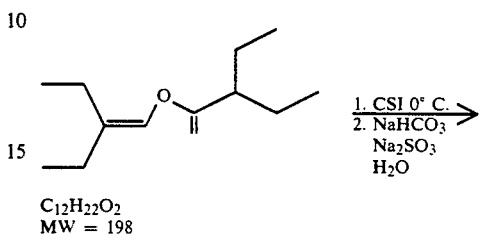

$C_{12}H_{22}O_2$
MW = 198

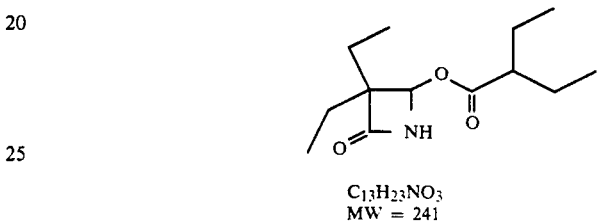

$C_{13}H_{23}NO_3$
MW = 241

|  | Amount | Mole | MW |
|---|---|---|---|
| Vinyl ester | 3.3 kg | 16.7 | 198 |
| Chlorosulfonyl isocyanate (d = 1.626) | 2.1 L | 24.2 | 141 |
| Toluene | 6.5 L |  |  |
| Solid NaHCO$_3$ | 13 kg | 155 | 84 |
| Solid Na$_2$SO$_3$ | 7.5 kg | 59.5 | 126 |
| Ethyl acetate | 20 L |  |  |
| Celite | 1.8 kg |  |  |
| Water | 70 L |  |  |
| Brine | 8 L |  |  |

The vinyl ester is charged into a 22 L vessel equipped with an overhead stirrer and an $N_2$ inlet. To the vinyl ester at +5° C. is added chlorosulfonyl isocyanate (2.1 L) over 1 hour. The mixture is stirred at +8° C. under nitrogen. After 45 hours the reaction is cooled to 0° C., and then diluted with toluene (5 L). The mixture is pumped into an open 250 L vessel containing D.I. water (60 L), ice (20 L), solid NaHCO$_3$ (13 kg) and solid Na$_2$SO$_3$ (7.5 kg). The mixture is stirred at 20° C. for 4 h. The batch is filtered through celite (1.8 kg) and the celite is rinsed with EtOAc (7 L). The filtrates are combined and the organic layer removed. The aqueous layer is extracted with EtOAc (12 L). The combined organics are washed with brine (8 L) and concentrated in vacuo. Toluene (2 L) is added and the solution concentrated in vacuo to afford 4.57 kg of a light yellow oil (assay yield is 3.153 kg; 78%).

Step D: Preparation of Benzyl 4-(3,3-diethyl-4-oxo-2-azetidonyl)oxyl)-benzene-acetate $C_{13}H_{23}NO_3$
MW = 241

$C_{22}H_{25}NO_4$
MW = 367

|  | Amount | Mole | MW |
|---|---|---|---|
| Phenol | 2.6 kg (as is) | 10.74 | 242 |
| β-Lactam | 4.57 kg at 69% | 13.08 | 241 |
|  | purity = 3.15 kg |  |  |
| $K_2CO_3$ milled | 4.5 kg | 32.6 |  |
| DMF | 24 L |  |  |
| $H_2O$ | 2.8 L + 10 L |  |  |
| EtOAc | 38 L |  |  |
| 2N HCl | 30 L |  | 60 |
| Sat'd. $NaHCO_3$ | 25 L |  |  |
| Brine | 10 L |  |  |

The phenol (2.6 kg) is dissolved in DMF (20 L). Water (2.8 L), and milled $K_2CO_3$ (4.5 kg) are then added. The mixture is cooled to +35° C. and the β-lactam (3.15 kg) is added as a solution in DMF (4 L). The temperature drops to +31° C. and the mixture is stirred at 30°–31° C. under $N_2$ for 1 hour. The reaction is cooled to +18° C. over 1 hour then is quenched with 2N HCl (15 L) and EtOAc (15 L). The mixture is pumped into a 250 liter extractor. The reaction flask, is rinsed with 2N HCl (15 L) and EtOAc (15 L). This is pumped into the extractor.

The organic layer is separated and the aqueous phase (pH=8.2) is extracted with EtOAc (18 L). The combined organic extracts are washed with saturated $NaHCO_3$ (13 L), D.I. $H_2O$ (10 L) and brine (10 L). The solvent is removed in vacuo to afford 5.4 kg of a yellow-orange oil.

Step E: Preparation of 4-(3,3-diethyl-3-oxo-2-azetidinyl)oxyl)-benzene acetic acid $C_{22}H_{25}NO_4$
MW = 367

$C_{15}H_{19}O_4N$
MW = 277

|  | Amount | Mole | MW |
|---|---|---|---|
| Benzyl ester | 5.4 kg (as is) | 10.35 | 365 |
|  | 3.8 kg (assay) |  |  |
| EtOH (punctilious) | 24 L |  |  |
| Cyclohexene | 7 L |  |  |
| 5% Pd/C | 403 gm |  |  |
| Solka floc | 1.2 kg |  |  |
| 10% $K_2CO_3$ | 9 L |  |  |
| EtOAc | 25 L |  |  |
| 6N HCl | 1.7 L |  |  |
| D.I. water | 5 L |  |  |
| MeOH | 0.7 L |  |  |

Dissolve the benzyl ester is EtOH (20 L) and cyclohexene (7 L), and add the Pd/C (403 gm) and EtOH (4 L). The reaction is heated to reflux (70° C.) for 30 min. The reaction is cooled to +30° C. over 2 hours, then filtered through SOLKA FLOC (1.2 kg). The cake and flask are washed with EtOAc (8 L). The filtrate is concentrated in vacuo, to afford a light yellow oil. The crude acid is dissolved into EtOAc (8 L) and partitioned into 10% $K_2CO_3$ (8 L). The organic phase is separated and the aqueous phase is extracted with EtOAc (5 L). The combined EtOAc extracts are washed with 10% $K_2CO_3$ (1 L). The combined $K_2CO_3$ washes are adjusted to pH=1.6 using 6N HCl (1.7 L total). The acidified aqueous phase is extracted with EtOAc (2×5 L) and the combined EtOAc extracts are washed with D.I. $H_2O$ (4 L).

The organic phase is concentrated in vacuo, then diluted with EtOAc (2 L) and reconcentrated. This affords 3.1 kg of a pale yellow oil.

Step F: Resolution of (+) 4-((3,3-dimethyl-4-oxo-2-azetidinyl)oxy)benzene acetic acid $C_{15}H_{19}O_4N$
MW = 277

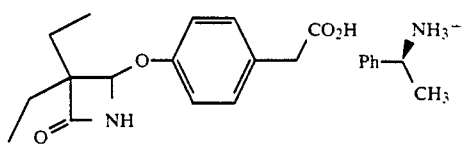

C₂₃H₃₀O₄N₂
MW = 398

|  | Amount | Mole | MW |
|---|---|---|---|
| Acid | 253 gm | 0.91 | 277 |
| R(+)-a-methylbenzylamine (d = 0.940) | 117.7 mL | 0.91 | 122 |
| S(−)-a-methylbenzylamine | 87.6 mL | 0.67 |  |
| EtOAc | 5.2 L |  |  |
| 2N HCl | 1.05 L |  |  |
| Brine | 0.35 L |  |  |

The racemic acid (253 gm) is dissolved in ethyl acetate (1.27 L) and treated with R(+)-α-methylbenzylamine (117.7 mL). The solution is seeded with pure (R R) salt. The resulting mixture is stirred at +23° C. for 18 h and then cooled to 0°-5° C., for 1 hour. The mixture is filtered, washed with cold ethyl acetate (2×150 mL) and dried. This affords 124 gm of the salt. The salt is then slurried with ethyl acetate (1.2 L) at 60° C. for 1 hour. The mixture is cooled to 0° C. for 1.5 hours, filtered, washed with ethyl acetate (2×150 mL) and dried in vacuo at 40° C. to afford 91 gm of the (R R) salt. All filtrates are combined and washed with 2N HCl solution (3×350 mL). The organic layer is concentrated to a viscous oil in vacuo. The oil is dissolved in ethyl acetate (935 mL) and treated with S(−)-α-methylbenzylamine (87.6 mL) as described above to afford the (S S) salt (119 gm).

Step G: Preparation of allyl-4-((3,3-diethyl-4-oxo-2-azetidinyl)oxy)benzene acetate

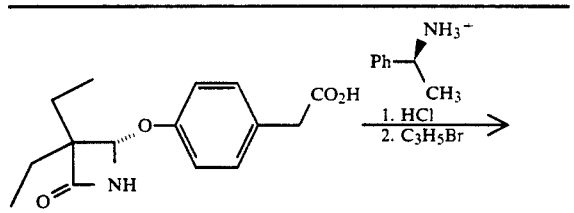

C₂₃H₃₀O₄N₂
MW = 398

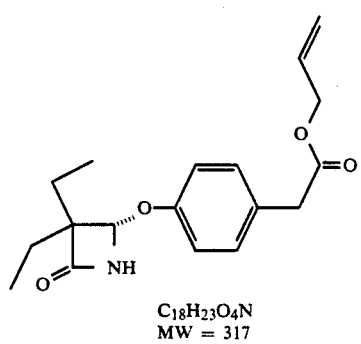

C₁₈H₂₃O₄N
MW = 317

|  | Amount | Mole | MW |
|---|---|---|---|
| Salt | 80 gm | 0.201 | 398 |
| Ethyl Acetate | 1.3 L |  |  |
| 2N HCl | 0.3 L |  |  |
| Allyl Bromide (d = 1.398) | 25.8 mL | 0.298 | 121 |
| Potassium Carbonate | 30.1 gm | 0.218 | 138 |
| Dimethylformamide | 300 mL |  |  |
| Water | 0.66 L |  |  |
| Sat'd NaHCO₃ | 360 mL |  |  |
| 0.05N HCl | 1.1 L |  |  |

The acid salt (80 gm) is partitioned between ethyl acetate (570 mL) and 2N HCl (92 mL) and the mixture stirred for 20-30 minutes. The aqueous layer is removed and the organic layer is washed with 2N HCl (2×91 mL). The ethyl acetate solution is concentrated in vacuo to afford 62.2 grams of a viscous oil. The oil is dissolved in DMF (300 mL) and charged into a 1 liter, 3-neck flask fitted with a temperature sensor and a mechanical stirrer. To the mixture is added potassium carbonate (30.1 gm) and allyl bromide (25.8 mL). The reaction is stirred for 5 h, then partitioned between ethyl acetate (360 mL) and water (360 mL). The aqueous layer is removed and extracted with ethyl acetate (360 mL). The combined organic layers are washed with saturated NaHCO₃ (2×180 mL), water (2×150 mL), and 0.05N HCl (3×360 mL). The ethyl acetate is removed in vacuo to afford 67.6 gm of an oil, which is 78% pure by weight. The yield of product is 52.7 gm (83%).

EXAMPLE 2

(R)-5-[(1-Isocyanato)butan-1-yl]benzo[β]furan

Step A: (4-Bromo-2-formyl)phenoxyacetic acid. Monohydrate

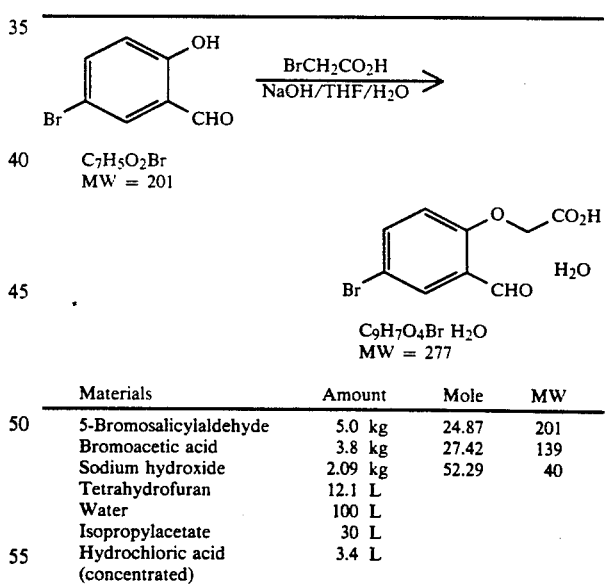

| Materials | Amount | Mole | MW |
|---|---|---|---|
| 5-Bromosalicylaldehyde | 5.0 kg | 24.87 | 201 |
| Bromoacetic acid | 3.8 kg | 27.42 | 139 |
| Sodium hydroxide | 2.09 kg | 52.29 | 40 |
| Tetrahydrofuran | 12.1 L |  |  |
| Water | 100 L |  |  |
| Isopropylacetate | 30 L |  |  |
| Hydrochloric acid (concentrated) | 3.4 L |  |  |

To a solution of 5-bromosalicylaldehyde (5.0 kg, 24.87 mol) in tetrahydrofuran (12.1 L) at 40° C. under a nitrogen atmosphere is added a solution of bromoacetic acid (3.8 kg, 27.42 mol) in water (50 L). The mixture is stirred at 40° C. and a solution of sodium hydroxide (2.09 kg, 52.29 mmol) in water (8.1 L) added over 20 min. The deep red solution is warmed to gentle reflux for 18 hours.

Tetrahydrofuran (~7 L) is distilled from the reaction mixture at atmospheric pressure and the resultant yellow solution cooled to room temperature (25° C.). The pH is adjusted to 8±0.2 by addition of saturated sodium bicarbonate solution. The resultant mixture is extracted with isopropylacetate (2×15 L) and the aqueous layer acidified to pH 3±0.2 with concentrated hydrochloric acid (2.4 L). The resultant slurry is aged at 20° C. for 1 hour, filtered, and the cake washed with water (7 L). The product is air dried for 3 hours, and in vacuo overnight to give the product as a pale yellow solid (3.77 Kg, 55% yield).

Step B: 5-Bromobenzofuran

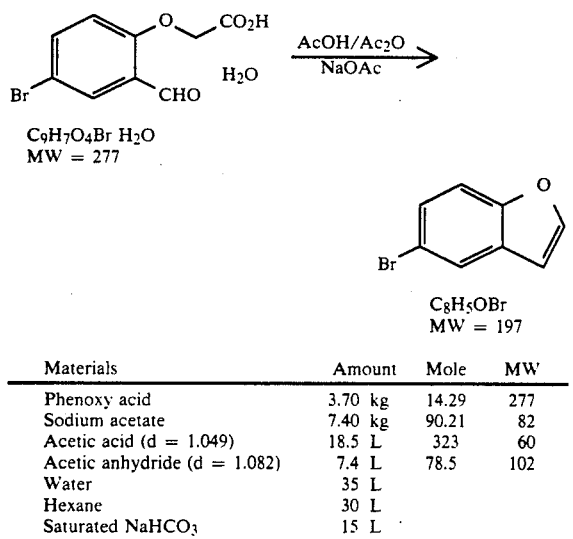

| Materials | Amount | Mole | MW |
|---|---|---|---|
| Phenoxy acid | 3.70 kg | 14.29 | 277 |
| Sodium acetate | 7.40 kg | 90.21 | 82 |
| Acetic acid (d = 1.049) | 18.5 L | 323 | 60 |
| Acetic anhydride (d = 1.082) | 7.4 L | 78.5 | 102 |
| Water | 35 L | | |
| Hexane | 30 L | | |
| Saturated NaHCO$_3$ | 15 L | | |

A slurry of the phenoxy acid (3.70 kg, 14.29 mol), and sodium acetate (7.40 kg, 90.21 mol) in acetic acid (18.5 L) is heated to gentle reflux under a nitrogen atmosphere. Acetic anhydride (7.4 L, 78.5 mol) is added dropwise over 6 hours. The reaction mixture is heated at reflux until HPLC indicates no remaining starting material.

The reaction is cooled to 80° C. and water (11.1 L) added dropwise over 1 hour. The mixture is reheated to gentle reflux for 1 hour, cooled to 25° C. and transferred to a separating funnel. Water (15 L) and hexane (15 L) are added, the phases separated and the lower aqueous layer re-extracted with hexane (15 L). The combined organics are washed with water (2×10 L), sat'd sodium bicarbonate solution (15 L) and dried (Na$_2$SO$_4$). Solvent evaporation affords 5-bromobenzofuran, 2.40 kg, 85%.

Step C: Preparation of 5-Formylbenzo[β]furan

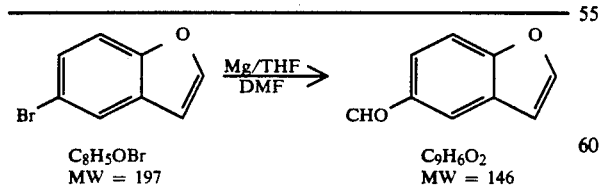

| Materials | Amount | Mole | MW |
|---|---|---|---|
| Bromobenzofuran | 90 gm | 0.45 | 197 |
| Magnesium | 11.44 gm | 0.48 | 24 |
| Iodine | 0.12 gm | 0.0005 | 254 |
| Dimethylformamide (d = 0.944) | 45 mL | 0.58 | 73 |
| THF | 120 mL | | |
| 3N HCl | 300 mL | | |

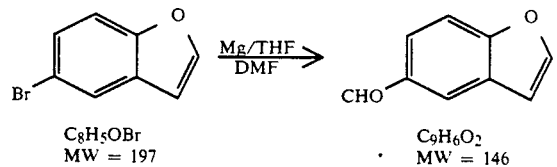

| Materials | Amount | Mole | MW |
|---|---|---|---|
| 2N HCl | 100 mL | | |
| Brine | 350 mL | | |
| EtOAc | 350 mL | | |

A slurry of powdered magnesium (11.44 gm) and iodine (0.12 gm) in THF (120 mL) is heated to 50° C., under N$_2$, for 0.5 hours. A 30 mL portion of the bromide (90 gm) in THF (225 mL) is added to the magnesium slurry at 50° C. (without stirring). The mixture is aged for 0.5 h then the remaining solution of the bromide is added over 1.5 hours (with stirring), while maintaining a gentle reflux. Once the addition is complete the solution of the Grignard is aged at 50° C. for 1 hour. The resulting dark solution is cooled to +5° C. and neat DMF (45 mL) is added dropwise over 30 minutes while maintaining the reaction temperature between +5° to +10° C. The mixture is aged at +10° C. for 1 hour and then cooled to +5° C. To the reaction is added 3N HCl (300 mL) and a 50% saturated solution of brine (225 mL) while maintaining the reaction temperature <15° C. Once the pH of the aqueous layer falls to pH=6, ethyl acetate (200 mL) is added and the remaining 3M HCl/brine mixture is added (final pH=1.2). The mixture is stirred for 1 hour. The aqueous layer is removed and extracted with ethyl acetate (150 mL). The combined organics are washed with 2N HCl (100 mL) and brine (3×80 mL). The organic layer is dried (Na$_2$SO$_4$) and concentrated to afford 63.6 gm (96%) of an orange oil.

Step D: Preparation of (S)-1-(Benzo[β]furan-5-yl)-1-butanol

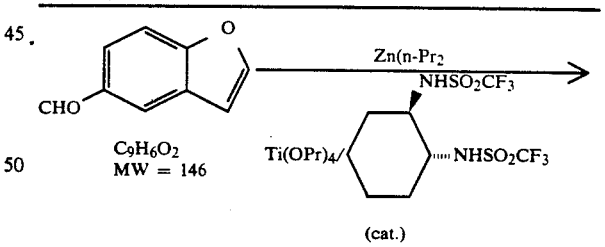

| Materials | Amount | Mole | MW |
|---|---|---|---|
| Aldehyde | 40 gm | 0.273 | 146 |
| Di-n-proplyzinc (d = 1.080) | 52 mL | 0.371 | 151 |
| Di-triflamide | 1.92 gm | 0.0051 | 378 |
| Titanium tetra-isopropoxide (d = 0.955) | 15 mL | 0.050 | 284 |
| Hexane | 400 mL | | |
| Toluene | 230 mL | | |

| | |
|---|---|
| 2N HCl | 600 mL |
| EtOAc | 250 mL |
| Brine | 300 mL |

To the di-triflamide (1.92 g) in dry toluene (80 mL) at 23° C. under $N_2$ is added titanium tetraisopropoxide (15 mL) in one portion and the slurry is warmed to 40° C. for 20 minutes, then cooled to 0° C.

In a separate vessel is added di-n-propylzinc (52 mL) to dry hexane (400 mL). The resulting homogenous solution is added to the solution of the triflamide while maintaining the temperature between −5° C. and 0° C. To the mixture at 0° C. is added a solution of the aldehyde (40 gm) in toluene (150 mL) over 30 minutes. The resulting yellow mixture is stirred at 0° C. for 18 hours. The resulting red mixture is cooled to −5° C. and quenched with 2N HCl (500 mL) over 1.5 hours while maintaining the reaction temperature between −5° C. to 0° C. for 1.2 hours. To the mixture is added ethyl acetate (100 mL) and the aqueous layer removed. The aqueous is extracted with ethyl acetate (150 mL) and the combined organics washed with 2N HCl (100 mL) and brine (2×150 mL). The organic layer is dried ($Na_2SO_4$) and concentrated to afford 50 gm of a yellow oil which solidifies on standing. The optical purity of this material is 95.5% ee.

Step E: Preparation of (R)-1-(Benzo[β]furan-5-yl)-1-aminobutane

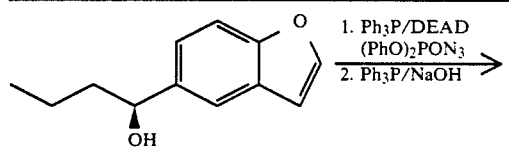

$C_{12}H_{14}O_2$
MW = 190

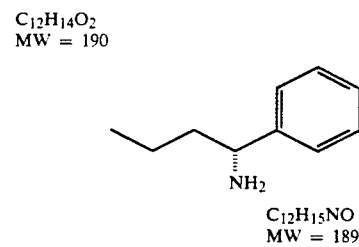

$C_{12}H_{15}NO$
MW = 189

| Materials | Amount | Mole | MW |
|---|---|---|---|
| Alcohol | 47.7 g | 0.251 | 190 |
| Triphenylphosphine | 228.5 g | 0.872 | 262 |
| Diethyl azodicarboxylate (d = 1.106) | 79.2 mL | 0.503 | 174 |
| Diphenylphosphoryl azide (d = 1.277) | 54.2 mL | 0.251 | 275 |
| THF | 1380 mL | | |
| 50% NaOH | 20 mL | | |
| 20% NaOH | 580 mL | | |
| 2N HCl | 90 mL | | |
| Sat'd Brine | 1000 mL | | |
| t-Butylmethylether | 1000 mL | | |
| Diethylether | 200 mL | | |
| Silica gel | 1.5 kg | | |
| Hexane | 4000 mL | | |
| Ethyl acetate | 1200 mL | | |
| Triethylamine | 160 mL | | |

To a solution of triphenylphosphine (132.3 gm) in THF (960 mL) at 0° C. is added ethyl azodicarboxylate (79.2 mL). The resulting solution is stirred at 0° C. until a thick slurry is obtained. To the slurry at 0° C. is added diphenylphosphoryl azide (54.2 mL) in one portion. To this mixture is added a solution of the alcohol (47.7 gm) in THF (125 mL) over 1.5 hours while maintaining the reaction temperature between −3° to −2° C. The resulting homogeneous solution is stirred at 0° C. for 0.5 hours. To this mixture is added triphenylphosphine (96.2 gm) in one portion and the solution is allowed to warm to +23° C. over 1 hour. The mixture is warmed to +50° C. for 2.5 hours. To the mixture is added 20% aqueous NaOH (580 mL) and the reaction stirred at 50° C. for 1 hour. The two phase mixture is cooled to +23° C. and the lower aqueous layer separated and extracted with THF (300 mL). The combined organics are washed with brine (2×500 mL) and concentrated in vacuo to afford 460 gm of an orange oil. The oil is dissolved in t-butyl-methylether (1 L) and allowed to stand for 18 hours. The mixture is filtered and the cake washed with MTBE (100 mL). The filtrates are concentrated in vacuo to afford 302 gm of an orange oil. The oil is further purified by silica gel chromatography. The oil is loaded on silica gel (1.5 kg of 60-200 mesh) and then eluted with 1:1 hexane:ethyl acetate (8 L) followed by pure ethyl acetate (4 L), then ethyl acetate containing 1% triethylamine. The fractions containing product (and triphenylphosphine oxide) are concentrated in vacuo. The resulting oily residue is swished with 5:1 hexane:ethyl acetate (200 mL) and filtered. The filtrates are concentrated in vacuo to afford 35.3 gm of an oil. The oil is dissolved in ethyl acetate (80 mL) and washed with 2N HCl (2×45 mL). The acidic aqueous layer is cooled to +5° C. then neutralized with 50% NaOH, (20 mL) and extracted with diethyl ether (2×50 mL). The organic layer is dried ($Na_2SO_4$) and concentrated in vacuo to afford 20.3 gm (45%) of an orange oil. The optical purity of this material is 88% ee.

Step F: (R)-5-[(1-Isocyanato)butan-1-yl]benzo[β]furan

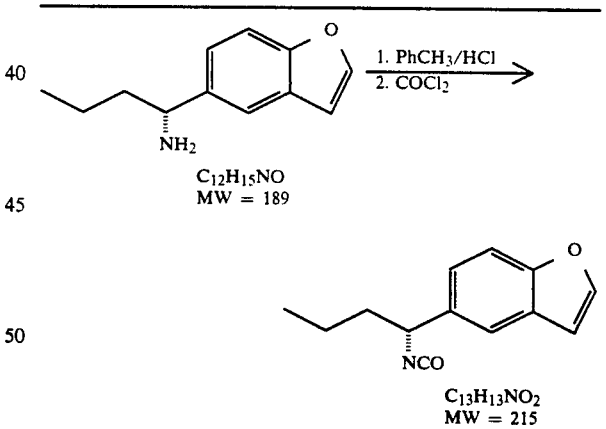

$C_{12}H_{15}NO$
MW = 189

$C_{13}H_{13}NO_2$
MW = 215

| Materials | Amount | Mole | MW |
|---|---|---|---|
| (R)-1-(Benzo[β]furan-5-yl)-1-butylamine (ee = 88%) | 19.2 g | 0.10 | 189 |
| Toluene | 392 mL | | |
| Conc. Hydrochloric acid | 12.7 mL | 0.15 | |
| Phosgene in toluene (1.93 M) | 150 mL | 0.29 | |
| Ethyl acetate | 300 mL | | |
| Saturated NaHCO$_3$ | 400 mL | | |
| Saturated brine | 200 mL | | |

To a solution of (R)-1-(benzofuran-5-yl)-1-butylamine (19.2 g, 0.10 mol) in toluene (192 mL) at room temperature is added concentrated hydrochloric acid (12.7 mL, 0.15 mol) dropwise, maintaining the reaction temperature between 20°-25° C. The white viscous slurry is stirred for 30 min at 20° C. Toluene (200 mL) is added and the slurry heated at reflux with azeotropic removal of water.

The dried slurry is cooled to 100° C. and a solution of phosgene in toluene (1.93M, 150 ml, 0.29 mol) added slowly over 1 hour. After a further 1 hour complete solution is obtained.

The solution is cooled to 10° C. and saturated sodium bicarbonate (200 ml) added followed by ethyl acetate (300 mL). The organic layer is separated and washed with saturated sodium bicarbonate (200 mL), brine (200 mL) and dried (Na$_2$SO$_4$). Evaporation of solvents gives the isocyanate 21.5 g, 98% as an orange oil.

EXAMPLE 3

(4S, 1R) 4[3,3-Diethyl-1-{1'-(benzo[β]furan-5-yl)-butylaminocarbonyl}-2-oxo-4-azetidinyl]oxybenzeneacetic acid Step A: (4S, 1R) 2-Propenyl 4[3,3-Diethyl-1-{1-(benzo[β]furan-5-yl)butylaminocarbonyl}-2-oxo-4-azetidinyl]oxybenzeneacetate

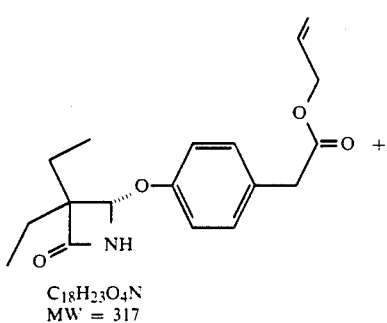

C$_{18}$H$_{23}$O$_4$N
MW = 317

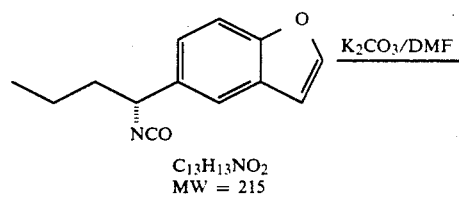

C$_{13}$H$_{13}$NO$_2$
MW = 215

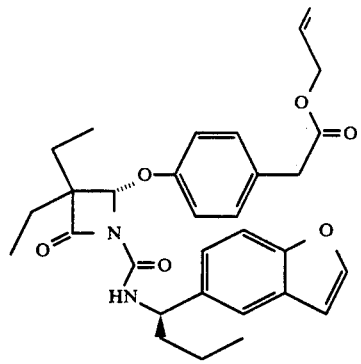

| Materials | Amount | Mmol | MW |
| --- | --- | --- | --- |
| Allyl ester (ee = 98.6%) | 26.5 g | 83.7 | 317 |
| Isocyanate (ee = 88%) | 19.0 g | 88.4 | 215 |
| Dimethylformamide | 150 mL | | |
| Potassium carbonate | 1.22 g | 8.84 | 136 |
| Ethyl acetate | 250 mL | | |
| 2N Hydrochloric acid | 200 mL | | |
| 0.1N Hydrochloric acid | 200 mL | | |
| Brine | 200 mL | | |

To a solution of the isocyanate (19.0 g, 88.4 mmol) in DMF (50 mL) at room temperature is added the allyl ester (1) (26.5 g, 83.7 mmol) in DMF (100 mL). Potassium carbonate (1.22 g, 8.84 mmol) is added and the slurry stirred for 1 hour.

The reaction mixture is partitioned between ethyl acetate (250 mL) and 2N hydrochloric acid (100 mL). The organic layer is separated and washed sequentially with 2N hydrochloric acid (100 mL), 0.1N hydrochloric acid (2×100 mL), brine (2×100 mL) and the solvents evaporated to give 52.8 g of the coupled product (de=85%).

Step B: (4S,1R)4[3,3-Diethyl-1{1'-(benzo[β]furan-5-yl)butylaminocarbonyl}-2-oxo-4-azetidinyl]oxybenzeneacetic acid

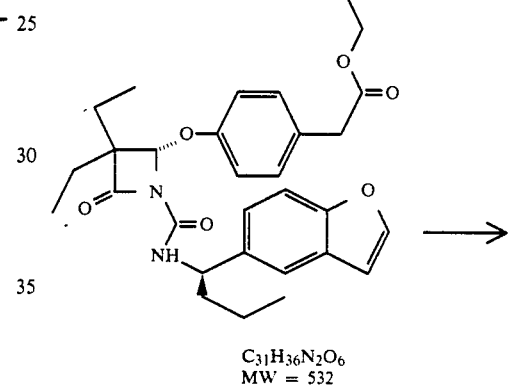

C$_{31}$H$_{36}$N$_2$O$_6$
MW = 532

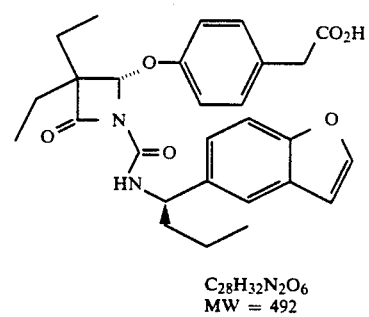

C$_{28}$H$_{32}$N$_2$O$_6$
MW = 492

| Materials | Amount | Mmol | MW |
| --- | --- | --- | --- |
| Allyl Ester | 10.0 g | 18.8 | 532 |
| Dimethylformamide | 180 mL | | |
| 10% Palladium on Charcoal | 2.0 g | | |
| Ammonium formate solution (55% wt/wt) | 15 mL | 133 | 63 |
| 1N Hydrochloric acid | 100 mL | | |
| Ethyl acetate | 200 mL | | |
| 0.1N Hydrochloric acid | 200 mL | | |
| Brine | 200 mL | | |

To a solution of the allyl ester (10.0 g, 18.8 mmol) in DMF, (150 mL) at 20° C. under a nitrogen atmosphere, is added 10% palladium on carbon (2.0 g). To the black slurry is added a 55% solution of ammonium formate in water (15.0 mL) over 30 min. The mixture is warmed to 45° C. for 30 min. The reaction mixture is cooled to 20°

C., filtered and the residue washed with DMF (30 mL). The filtrates are partitioned between 1N hydrochloric acid (100 mL) and ethyl acetate (200 mL). The organic extract is separated and washed with 0.1N hydrochloric acid (2×100 mL) and brine (2×100 mL). Evaporation of the solvent gives a pale yellow viscous gum, 9.25 g, 100% yield.

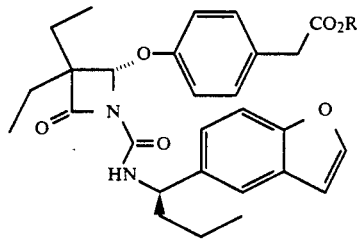

R = H C$_{28}$H$_{32}$N$_2$O$_6$ (MW = 492)

R = H$_3$NC(CH$_2$OH)$_3$ C$_{32}$H$_{44}$N$_3$O$_9$ (MW = 614)

| Materials | Amount | Mmole | MW |
|---|---|---|---|
| Acid | 39.0 g | 79.3 | 492 |
| Tris-(hydroxymethyl) aminomethane | 9.6 g | 79.3 | 121 |
| Isopropanol | 500 mL | | |
| Hexanes | 2000 mL | | |
| Isopropanol/Hexanes (1:4) | 80 mL | | |

A slurry of the acid (39.0 g, 79.3 mmol) and tris-(hydroxymethyl)aminomethane (9.6 g, 79.3 mmol) in isopropanol (500 mL) is warmed to 60° C. to complete dissolution. Hexanes (1.3 L) are added dropwise to give a slightly cloudy mixture. The mixture is seeded with L-683,845-tris salt (200 mg) and allowed to cool to 20° C. overnight. Hexanes (700 mL) are added and the slurry aged at 5° C. for 2 hours, filtered and the product washed with isopropanol/hexanes (1:4, 80 mL). The product is dried in vacuo at 20° C. to give 29.9 g (61.5%) of the title compound.

What is claimed is:

1. A process intermediate selected from the group consisting of B, C and D, which are

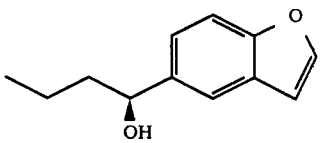

B

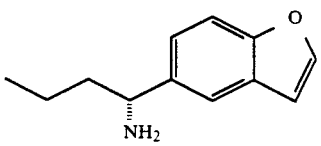

C and,

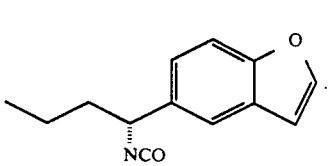

D

* * * * *